(12) United States Patent
Zhong et al.

(10) Patent No.: US 11,591,354 B2
(45) Date of Patent: Feb. 28, 2023

(54) THIAMINE COMPOUND, PREPARATION METHOD AND PHARMACEUTICAL COMPOSITION THEREOF

(71) Applicant: SHANGHAI RAISING PHARMACEUTICAL CO., LTD., Shanghai (CN)

(72) Inventors: Chunjiu Zhong, Shanghai (CN); Huan Zhang, Shanghai (CN)

(73) Assignee: SHANGHAI RAISING PHARMACEUTICAL CO., LTD., Shanghai (CN)

(*) Notice: Subject to any disclaimer, the term of this patent is extended or adjusted under 35 U.S.C. 154(b) by 0 days.

(21) Appl. No.: 17/298,214

(22) PCT Filed: Nov. 26, 2019

(86) PCT No.: PCT/CN2019/120942
§ 371 (c)(1),
(2) Date: May 28, 2021

(87) PCT Pub. No.: WO2020/108478
PCT Pub. Date: Jun. 4, 2020

(65) Prior Publication Data
US 2022/0089621 A1 Mar. 24, 2022

(30) Foreign Application Priority Data
Nov. 28, 2018 (CN) .......................... 201811435584.X

(51) Int. Cl.
*C07F 9/6512* (2006.01)
(52) U.S. Cl.
CPC .................. *C07F 9/6512* (2013.01)
(58) Field of Classification Search
CPC .................................................... C07F 9/6512
See application file for complete search history.

(56) References Cited

U.S. PATENT DOCUMENTS

| 7,932,240 B2* | 4/2011 | Dousson ............... A61P 43/00 |
| | | 514/80 |
| 10,947,258 B1* | 3/2021 | Zhong .................. C07F 9/6512 |
| 2021/0163515 A1* | 6/2021 | Zhong .................. C07F 9/6512 |

FOREIGN PATENT DOCUMENTS

| CN | 103772432 A | 5/2014 |
| CN | 109111478 A | 1/2019 |
| EP | 2918593 A1 | 9/2015 |
| GB | 1264580 A | 2/1972 |
| JP | S39-021372 B | 9/1964 |
| JP | S39-021526 B | 10/1964 |
| JP | S40-001396 B | 1/1965 |
| JP | 2013-213027 A | 10/2013 |
| WO | WO 2020/108480 A1 | 6/2020 |
| WO | WO 2020/108481 A1 | 6/2020 |

OTHER PUBLICATIONS

Nagawa et al., CA 57:75914, 1962. (Year: 1962).*
Grant, R., Grant, C. (1987). Grant & Hackh's Chemical Dictionary (5th ed.). New York, NY: McGraw-Hill, p. 313. (Year: 1987).*
International Patent Application No. PCT/CN2019/120942; Int'l Search Report; dated Feb. 28, 2020; 2 pages.
Kataoka et al.; "S-Acylthiamine O-Disubstituted Phosphate"; Takamine Kenkyusho Nenpo; vol. 13; Dec. 1961; p. 24-27 (contains English Abstract).
European Patent Application No. 19888995.8; Extended Search Report; dated Jun. 29, 2022; 8 pages.
Nagawa et al.; "S-Acylthiamine O-Monophoshate"; Takamine Kenkyusho Nenpo; vol. 13; 1961; p. 20-23.

* cited by examiner

*Primary Examiner* — Laura L Stockton
(74) *Attorney, Agent, or Firm* — BakerHostetler

(57) ABSTRACT

The embodiments of the present invention provide a series of thiamine compounds having a hydrocarbon group

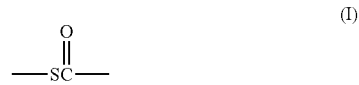

(I)

or a substituted hydrocarbon group attached at (I), wherein the compounds have an inhibitory effect on Aβ40 and/or Aβ42.

13 Claims, No Drawings

THIAMINE COMPOUND, PREPARATION METHOD AND PHARMACEUTICAL COMPOSITION THEREOF

CROSS-REFERENCE TO RELATED APPLICATIONS

This application is the national phase of International Application No. PCT/CN2019/120942, titled "THIAMINE COMPOUND, PREPARATION METHOD AND PHARMACEUTICAL COMPOSITION THEREOF", filed on Nov. 26, 2019, which claims priority to Chinese Patent Application No. 201811435584.X, titled "THIAMINE COMPOUND, PREPARATION METHOD AND PHARMACEUTICAL COMPOSITION THEREOF", filed on Nov. 28, 2018 with the China National Intellectual Property Administration, which foregoing applications are incorporated herein by reference in their entireties for any and all purposes.

TECHNICAL FIELD

The present disclosure generally relates to pharmaceutical and chemical industries, and more particularly, to a thiamine compound, a preparation method and a pharmaceutical composition thereof.

BACKGROUND

Alzheimer's disease (AD, commonly known as senile dementia) is a progressive neurodegenerative disease with the main clinical manifestations of cognitive and behavioral disorders; as the most common form of elderly senile dementia, AD is mainly characterized by cognitive impairment and rapid decline in memory function. Pathologically it is characterized by intracerebral β-amyloid (Aβ) deposits contributing to senile plaques, intracellular neurofibrillary tangles due to hyperphosphorylation of tau protein, impaired glucose metabolism, and neuronal/synaptic loss. Due to the long course of illness and poor self-care ability of patients, it brings serious mental stress and economic burden to the family and society. While there are no drugs capable of preventing or delaying the progression of the disease worldwide at present, and currently available drugs for treating AD only help with symptoms, and are able only to improve cognitive symptoms temporarily, and no treatment can stop or even slow the deterioration of the disease.

Studies have shown that by inhibiting the activity of glycogensynthasekinase-3 (GSK-3), benfotiamine may decrease beta-amyloid (Aβ) deposition and tau protein phosphorylation in the brain, and reduce pathological damage of alzheimer's disease. Thus, the synthetic methods and crystal forms of benfotiamine and use thereof in the treatment of Alzheimer's disease have been studied and reported successively. However, no relevant research on other phosphorthiamine compounds has been reported yet.

SUMMARY

An object of embodiments of the present disclosure is to provide a novel thiamine compound, a preparation method and a technical scheme of a pharmaceutical composition thereof.

A thiamine compound has a structure as shown in Formula (1) or Formula (2),

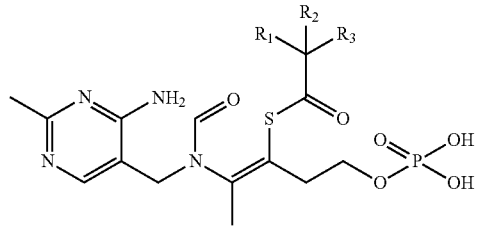

(1)

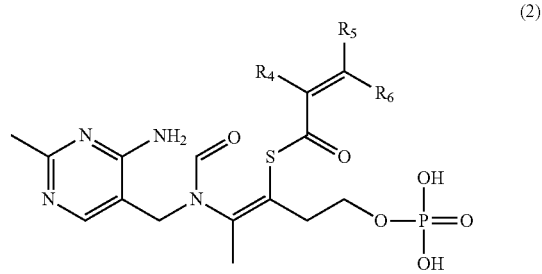

(2)

wherein $R_1$, $R_2$, $R_3$, $R_4$, $R_5$ and $R_6$ are each independently hydrogen atom, halogen atom, nitro, cyano, sulfo, amino, substituted amine group, ester group, carboxyl, hydroxyl, sulfydryl, hydrocarbylsulfydryl, hydrocarbyl, substituted hydrocarbyl, hydrocarbyloxy, substituted hydrocarbyloxy, acyl or acylamino.

Optionally, the thiamine compound has a structure as shown in Formula (1), wherein R1 and R2 are hydrogen atom, and R3 is a benzyl or a 1,5-difluorophenyl.

Optionally, the $R_1$, R2, R3, R4, R5 and R6 are each independently hydrogen atom or a C1-C18 hydrocarbyl.

Optionally, the thiamine compound has a structure as shown in Formula (1), wherein $R_1$ or $R_2$ is independently hydrogen atom, methyl or ethyl, and $R_3$ is C1-C10 hydrocarbyl.

Optionally, the thiamine compound has a structure as shown in Formula (1), wherein R1 is hydrogen atom, R2 is methyl, and R3 is methyl or ethyl.

Optionally, the thiamine compound has a structure as shown in Formula (1), wherein R1 is methyl, R2 is methyl and R3 is vinyl.

Optionally, the thiamine compound has a structure as shown in Formula (2), wherein R5 is hydrogen atom, and R4 is n-propyl.

Another object of embodiments of the present disclosure is to provide a preparation method of the thiamine compound. the thiamine compound is prepared by reacting thiamine phosphate shown in Formula (1a) with acyl chloride shown in Formula (1b) or (2b);

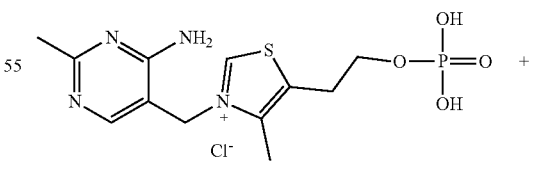

(1a)

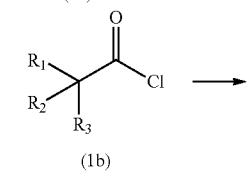

(1b)

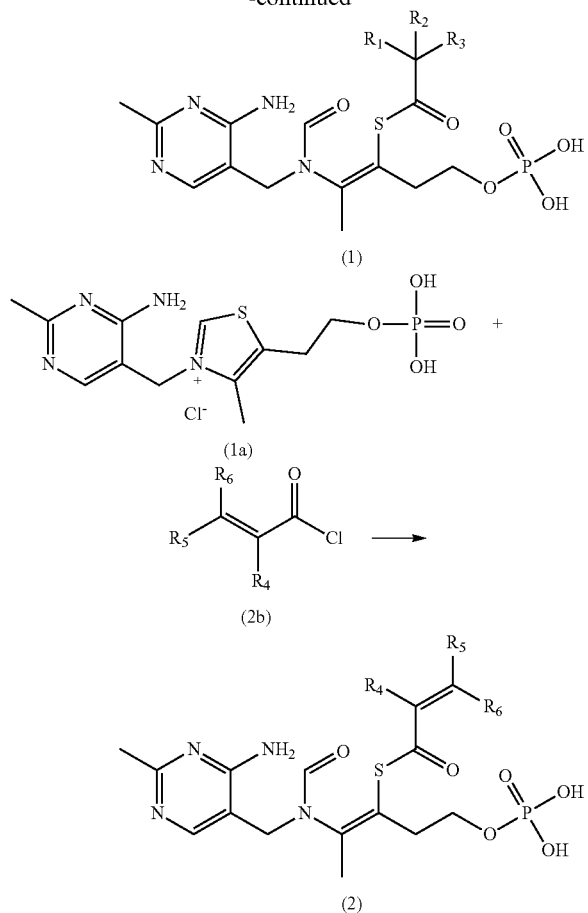

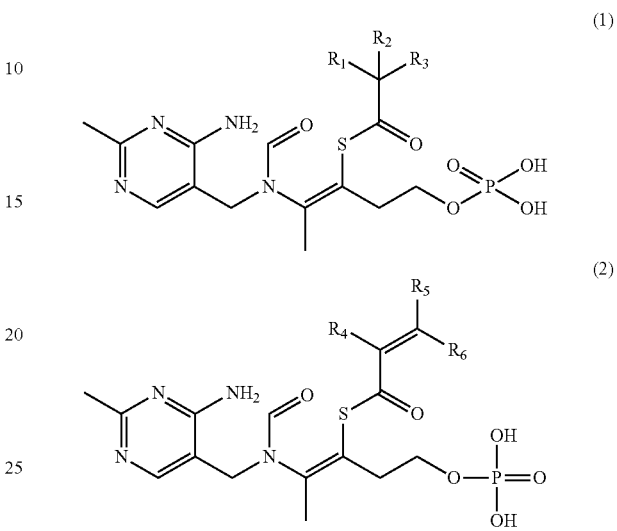

wherein R1, R2, R3, R4, R5 and R6 are each independently hydrogen atom, halogen atom, nitro, cyano, sulfo, amino, substituted amine group, ester group, carboxyl, hydroxyl, sulfydryl, hydrocarbylsulfydryl, hydrocarbyl, substituted hydrocarbyl, hydrocarbyloxy, substituted hydrocarbyloxy, acyl or acylamino.

Another object of embodiments of the present disclosure is to provide a pharmaceutical composition comprising any of the above thiamine compounds and isomers thereof or salts of the thiamine compounds and the isomers thereof.

Optionally, the pharmaceutical composition is used for the preparation of a medicament for preventing and treating neurodegenerative diseases.

Optionally, the pharmaceutical composition is used for the preparation of a medicament for preventing and treating Alzheimer's disease or aging.

Embodiments of the present disclosure may provide following advantages. Compared with the prior art, the embodiments of the present invention provide a series of thiamine compounds of Formula (1) or Formula (2), wherein the compounds have inhibitory effects on Aβ40 and/or Aβ42; further, when the thiamine compound has a structure as shown in Formula (1), $R_1$ is hydrogen atom, R2 is methyl, R3 is a methyl or ethyl, or R1 is methyl, R2 is methyl, R3 is vinyl or n-butyl, or the thiamine compound has a structure as shown in Formula (2), when R4 and R5 are hydrogen atom, and R6 is n-propyl, there was prominent inhibitory effects on Aβ40 and Aβ42.

DETAILED DESCRIPTION

The thiamine compound provided by the embodiments of the present invention has a structure as shown in Formula (1) or Formula (2)

wherein $R_1$, $R_2$, $R_3$, $R_4$, $R_5$ and $R_6$ are each independently hydrogen atom, halogen atom, nitro, cyano, sulfo, amino, substituted amine group, ester group, carboxyl, hydroxyl, sulfydryl, hydrocarbylsulfydryl, hydrocarbyl, substituted hydrocarbyl, hydrocarbyloxy, substituted hydrocarbyloxy, acyl or acylamino.

In a specific embodiments of the present invention, the substituents include linear, branched, or cyclic hydrocarbyl, which may be alkanyl or alkenyl, alkynyl, or arene groups; in some embodiments, the hydrocarbyl are alkanyl, specifically, such as methyl, ethyl, vinyl, propenyl, n-propyl, isopropyl, n-butyl, t-butyl, isobutyl, pentyl, 1-ethylpropyl, I-methylbutyl, cyclopentyl, hexyl, I-methylpentyl, I-ethylbutyl, cyclohexyl, 2-heptyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, and tricosyl; in some embodiments, the hydrocarbyl is arene groups, specifically, such as phenyl, 2-methylphenyl, 3-methylphenyl, 4-methylphenyl, 1-naphthyl, 2-naphthyl, benzyl or 2-phenylethyl.

In specific embodiments of the present invention, the substituted hydrocarbyl includes halogen atom substitution, nitro substitution, cyano substitution, sulfo substitution, alkoxy substitution, amine substitution, carboxyl substitution, hydroxyl substitution or sulfydryl substitution of the above-mentioned hydrocarbyl, specifically such as methoxyethyl, ethoxyethyl, butoxyethyl, trifluoromethyl, and pentafluoroethyl.

In a specific embodiment of the present invention, the hydrocarbyloxy includes linear, branched or cyclic hydrocarbyloxy, specifically, such as methoxy, ethoxy, n-propoxy, isopropoxy, n-butoxy, tert-butoxy, isobutoxy, pentoxy, 1-ethylpropoxy, 1-methylbutoxy, cyclopentoxy, hexoxy, 1-methylpentoxy, 1-ethylbutoxy, cyclohexyloxy, 2-heptyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, eicosanyloxy, heneicosanyloxy, docosanyloxy, tricosanyloxy, phenoxy, 2-methylphenoxy, 3-methylphenoxy, 4-methylphenoxy, 1-naphthyloxy, 2-naphthyloxy, benzyloxy or 2-phenylethoxy.

In specific embodiments of the present invention, the substituted hydrocarbyloxy includes halogen atoms substitution, nitro substitution, cyano substitution, sulfo substitution, hydrocarbyloxy substitution, amine substitution, carboxyl substitution, hydroxyl substitution or sulfydryl substitution of the above hydrocarbyloxy, specifically, such as methoxyethoxy, ethoxyethoxy, butoxyethoxy, trifluoromethoxy, and pentafluoroethoxy.

In a specific embodiment of the present invention, the hydrocarbylsulfydryl includes linear, branched or cyclic hydrocarbylsulfydryl, specifically, such as methylsulfydryl, ethylsulfydryl, n-propylsulfydryl, isopropylsulfydryl, n-butylsulfydryl, t-butylsulfydryl, isobutylsulfydryl, pentylsulfydryl, 1-ethylpropylsulfydryl, 1-methylbutylsulfydryl, cyclopentylsulfydryl, hexylsulfydryl, 1-methylpentylsulfydryl, 1-ethylbutylsulfydryl, cyclohexylsulfydryl, 2-heptanesulfydryll, heptanesulfydryl, octanesulfydryll, nonanesulfydryll, decylsulfydryl, undecylsulfydryl, dodecylsulfydryl, tridecylsulfydryl, tetradecylsulfydryl, pentadecylsulfydryl, hexadecylsulfydryl, heptadecylsulfydryl, octadecylsulfydryl, nonadecylsulfydryl, eicosanylsulfydryl, heneicosanylsulfydryl, docosanylsulfydryl, tricosanylsulfydryl, phenylsulfydryl, 2-methyl phenylsulfydryl, 3-methyl phenylsulfydryl, 4-methyl phenylsulfydryl, 1-naphthylsulfydryl, 2-naphthylsulfydryl, benzylsulfydryl or 2-phenylethylsulfydryl.

In specific embodiments of the present invention, the substituted hydrocarbylsulfydryl includes halogen atoms substitution, nitro substitution, cyano substitution, sulfo substitution, hydrocarbylsulfydryl substitution, amine substitution, carboxyl substitution, hydroxyl substitution or sulfydryl substitution of the above-mentioned hydrocarbylsulfydryl, specifically such as methoxyethanesulfydryl, ethoxyethansulfydryl, butoxyethansulfydryl, trifluoromethylsulfydryl, and pentafluoroethanesulfydryl.

In a specific embodiment of the present invention, the acyl includes various hydrocarbylacyl or various substituted hydrocarbylacyl, and the substitutions include halogen atoms substitution, nitro substitution, cyano substitution, sulfo substitution, amine substitution, carboxyl substitution, hydroxyl substitution or sulfydryl substitution, specifically such as formyl, acetyl, n-propionyl, iso-propionyl, n-butyryl, tert-butyryl, iso-butyryl, pentanoyl, 1-ethylpropionyl, 1-methylbutyryl, cyclopentanoyl, hexanoyl, 1-methylpentanoyl, 1-ethylbutanoyl, cyclohexanoyl, 2-heptanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, aralkanoyl, eicosanoyl, heneicosanoyl, docosanoyl, tricosanoyl, benzoyl, 2-methylbenzoyl, 3-methylbenzoyl, 4-methylbenzoyl, 1-naphthoyl, 2-naphthoyl, benzylformyl, 2-phenylacetyl, methoxyacetyl, ethoxyacetyl, butoxyacetyl, and trifluoroacetyl.

In a specific embodiment of the present invention, the ester group includes various hydrocarbyl ester group or various substituted hydrocarbyl ester group, and the substitution includes halogen atom substitution, nitro substitution, cyano substitution, sulfo substitution, amine substitution, carboxyl substitution, hydroxyl substitution or sulfydryl substitution, specifically such as methyl ester group, ethyl ester group, n-propyl ester group, isopropyl ester group, n-butyl ester group, t-butyl ester group, isobutyl ester group, pentyl ester group, 1-ethylpropyl ester group, 1-methylbutyl ester group, cyclopentyl ester group, hexyl ester group, 1-methylpentyl ester group, 1-ethylbutyl ester group, cyclohexyl ester group, 2-heptyl ester group, heptyl ester group, octyl ester group, nonyl ester group, decyl ester group, undecyl ester group, dodecyl ester group, tridecyl ester group, tetradecyl ester group, pentadecyl ester group, hexadecyl ester group, heptadecyl ester group, octadecyl ester group, nonadecyl ester group, aralkyl ester groups, eicosanyl ester group, heneicosanyl ester group, docosanyl ester group, tricosanyl ester group, benzyl ester group, 2-methylbenzyl ester group, 3-methylbenzyl ester group, 4-methylbenzyl ester group, 1-naphthylmethyl ester group, 2-naphthylmethyl ester group, benzyl methyl ester group, 2-phenethyl ester group, methoxyethyl ester group, ethoxyethyl ester group, butoxyethyl ester group or trifluoroethyl ester group.

In a specific embodiment of the present invention, the substituted amine group includes various hydrocarbyl-substituted amine group or various substituted hydrocarbyl-substituted amine group, and the substitution includes halogen atoms substitution, nitro substitution, cyano substitution, sulfo substitution, amine substitution, carboxyl substitution, hydroxyl substitution or sulfydryl substitution, specifically such as methylamino, ethylamino, n-propylamino, isopropylamino, n-butylamino, t-butylamino, isobutylamino, pentylamino, 1-ethylpropylamino, 1-methylbutylamino, cyclopentylamino, hexylamino, 1-methylpentylamino, 1-ethylbutylamino, cyclohexylamino, 2-heptylamino, heptylamino, octylamino, nonylamino, decylamino, undecylamino, dodecylamino, tridecylamino, tetradecylamino, pentadecylamino, hexadecylamino, heptadecylamino, octadecylamino, nonadecylamino, aralkylamino, eicosanylamino, heneicosanylamino, docosanylamino, tricosanylamino, benzylamino, 2-methylbenzylamino, 3-methylbenzylamino, 4-methylbenzylamino, 1-naphthylmethylamino, 2-naphthylmethylamino, benzylmethylamino, 2-phenylethylamino, methoxyethylamine, ethoxyethylamine, butoxyethylamine or trifluoroethylamino.

In a specific embodiment of the present invention, the acylamino includes various hydrocarbylacylamino or various substituted hydrocarbylacylamino, and the substitution includes halogen atom substitution, nitro substitution, cyano substitution, sulfo substitution, amido substitution, carboxyl substitution, hydroxyl substitution or sulfydryl substitution, specifically, such as formamido, acetamido, n-propylamido, isopropylamido, n-butyramido, tert-butyramido, isobutyramido, pentanamido, 1-ethylpropanamido, 1-methylbutanamido, cyclopentylamido, hexanamido, 1-methylpentanamido, 1-ethylbutanamido, cyclohexylamido, 2-heptanamido, heptanamido, octanamido, nonanamido, decanamido, undecylamido, dodecanylamido, tridecanamido, tetradecanamido, pentadecanamido, hexadecylamido, heptadecanamido, octadecylamido, nonadecanamido, aralkanylamido, eicosanylamido, heneicosanylamido, docosanylamido, tricosanylamido, benzamido, 2-methylbenzamido, 3-methylbenzamido, 4-methylbenzamido, 1-naphthylformamido, 2-naphthylformamide, benzylformamide, 2-phenylacetamido, methoxyacetamido, ethoxyacetamido, butoxyacetamido, and trifluoroacetamido.

In a specific embodiment of the present invention, the thiamine compound has a structure as shown in formula (1), R1 and R2 are hydrogen atom, and R3 is benzyl or 1,5 difluorophenyl.

In a specific embodiment of the present invention, R1, R2, R3, R4 and R5. R6 are each independently hydrogen atom or C1-C18 hydrocarbyl, preferably the thiamine compound has a structure as shown in Formula (1), R1 and R2 are each independently hydrogen atom or C1-C4 hydrocarbyl, and further R1 or R2 is independently hydrogen atom, methyl or ethyl, and R3 is a C1-C10 hydrocarbyl; it is further preferable that R1 is hydrogen atom, R2 is methyl, R3 is methyl or ethyl, or R1 is methyl, R2 is methyl, and R3 is vinyl in consideration of the inhibitory effect on Aβ40 and Aβ42; or preferably, the thiamine compound has a structure as shown in Formula (2), R4 and R5 are hydrogen atom, and R6 is n-propyl.

The present invention also provides a preparation method of the thiamine compound, which is prepared by reacting thiamine phosphate shown in Formula (1a) with acyl chloride shown in Formula (1b) or (2b);

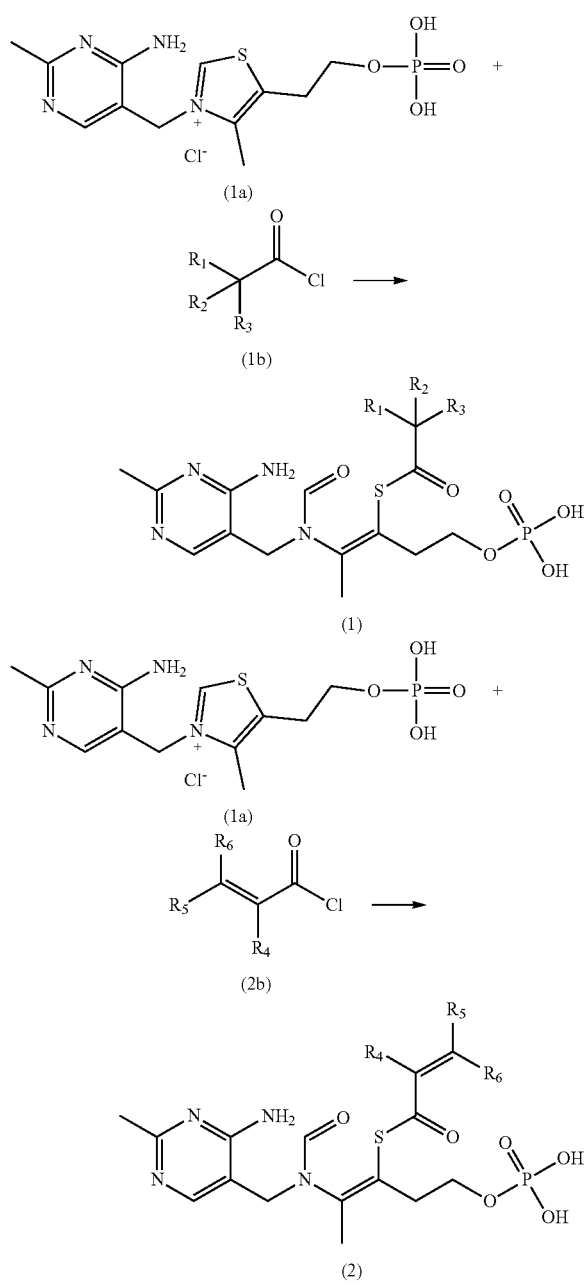

wherein R1, R2, R3, R4, and R5, R6 are each independently hydrogen atom, halogen atom, nitro, cyano, sulfo, amino, substituted amine group, ester group, carboxyl, hydroxyl, sulfydryl, hydrocarbylsulfydryl, hydrocarbyl, substituted hydrocarbyl, hydrocarbyloxy, substituted hydrocarbyloxy, acyl or acylamino.

In a specific embodiment of the preparation method of the thiamine compound in the present invention, specific experimental conditions can be conducted by referring to an experimental condition method (for the preparation of benfotiamine by reacting thiamine phosphate with benzoyl chloride) disclosed in the prior art as EP2918593A1, specifically, for example, the thiamine phosphate shown in Formula (1a) was dissolved in water, a 30% sodium hydroxide solution was added dropwise, and a pH value was adjusted to 10-12, followed by stirring for dissolving; an acyl chloride solution shown in Formula (1b) was added dropwise under 0-15° C., and the pH value was controlled and adjusted to 10-12 during the addition; the mixture was reacted for 0.5-3 h after the addition, and extracted and purified to give the thiamine compound. As for different acyl chlorides shown in Formula (1b), the reaction conditions can be conventionally selected and adjusted according to actual conditions, such as the selection of a solvent for the preparation of the acyl chloride solution shown in Formula (1b), and the selection of an extraction solvent.

Further, the present invention also provides a pharmaceutical composition including the above-mentioned thiamine compound and isomers thereof or salts of the thiamine compound and the isomers thereof, preferably a pharmaceutical composition for the preparation of a medicament for preventing and treating neurodegenerative diseases, and further preferably a pharmaceutical composition for the preparation of a medicament for preventing and treating Alzheimer's disease or aging. The salts are pharmaceutically acceptable salts such as lithium, sodium, potassium or calcium salts. The composition can be prepared into tablets, powders, sprays, water injection, powder injection, rectal suppositories, or skin patches (transdermal administration) according to conventional methods.

EXAMPLES

The test specification of the present invention is as follows:

Nuclear magnetic resonance ($^1$H NMR): NMR shifts (δ) were given in parts-per-million (ppm) units. NMR was conducted using a BrukeRAVANCE-500 instrument with deuterated dimethyl sulfoxide (DMSO-D6), deuterated methanol (CD3 OD), and deuterated water (D2O) as solvents, and tetramethylsilane (TMS) as an internal standard.

Mass Spectrometry (MS): MS analysis was conducted using an Agilent (ESI) mass spectrometer (Manufacturer: Agilent, Model: Agilent 6110).

1. Bioassay
1.1 Materials and Methods
(1) A BCA Protein Concentration Kit was purchased from Beyotime Biotechnology, a detection kit for Aβ40 and Aβ42 was purchased from Wako Co., Ltd., and cell culture related reagents were purchased from Gibico Co., Ltd.
(2) HEK293APP/sw overexpression cell culture: cells were cultured in a 48-well plate in DMEM culture medium (containing 10% FBS, 100 μg/mL G418 (Geneticin) and diabody), 4 mM stock solution of a test sample (prepared by dissolving the test sample in DMEM culture medium) was diluted to 400 μM in DMEM culture medium at a cell density of 70%, to each well was added 500 μL of the test sample, and the cells were cultured for 24 h.
(3) To the culture solution supernatant was added a BCA reagent, after incubating for 30 min at room temperature, absorbance of each well was measured at OD 570 nm with a microplate reader, and a total protein concentration was calculated according to a protein standard curve; concentrations of Aβ40 and Aβ42 were measured with supernatant: the supernatant was added into a coated 96-well plate, followed by incubating overnight at 4° C., the reagent was removed and washed, HRP (horseradish peroxidase) labeled antibody was added, followed by incubating for 2 h at 4° C., the reagent was removed and washed, a TMB color developing solution was added, followed by incubating for 30 min at room temperature, a stop solution was added to stop reaction, absorbance of each well was measured at OD 570 nm with a microplate reader, concentrations of Aβ40 and Aβ42 were calculated according to standard curves of A40 and Aβ42 respectively, and finally the concentrations of Aβ40 and Aβ42 were adjusted by using a total protein concentration to obtain a final concentration.

The compounds synthesized in the following Examples were based on the compounds as shown in the Formulas, and the Chinese and English names were used as references only.

Example 1

Synthesis of (Z)—S-(2-(N-((4-amino-2-methylpyrimidin-5-yl) methyl) formamido)-5-(phosphonooxy) pent-2-en-3-yl) butanethioate 1-1

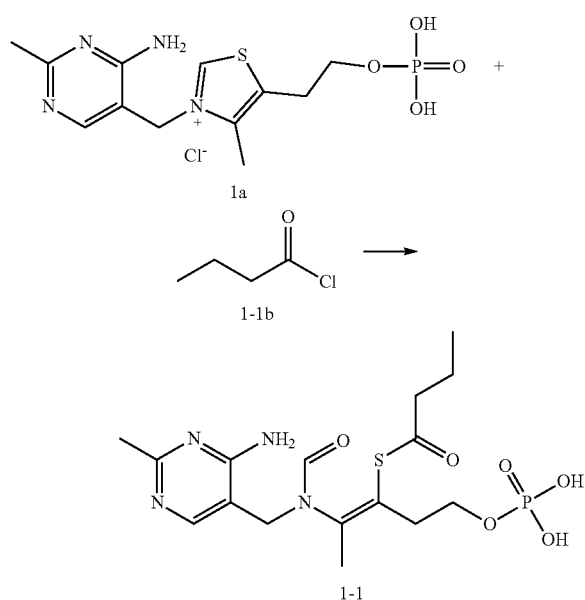

6.6 g of thiamine phosphate was dissolved in 8.0 g of water under stirring; a sodium hydroxide solution (30%) was added dropwise to adjust pH to 10-12; after stirring for 0.5 h, the pH was measured again, and adjusted to 10-12 until the pH was stable, followed by stirring for 1 h; 2.3 g of a dichloromethane solution of Formula 1-b was added dropwise over a period of time at 10° C.; liquid separation was conducted, a dichloromethane phase was dried over anhydrous sodium sulfate, followed by spin-drying dichloromethane to yield a yellow oily liquid, 2 mL of methanol was added for dissolved clarification, followed by 30 mL of ethyl acetate; the mixture was stirred to separate out a solid, then filtered to obtain a filter cake, which was dried at 45° C. to give the product 1-1.

The product 1-1 was subjected to $^1$H NMR and MS tests, and the results were as follows. A test sample stock solution prepared from the product 1-1 was subjected to a bioassay, and the results were shown in Table 1.

MS m/z (ESI): 433.2 [M$^{+1}$]

$^1$H NMR (DMSO-d6) δ 7.84 (s, 1H), 7.81 (s, 1H), 4.47 (s, 2H), 3.78-3.82 (m, 2H), 2.51-2.61 (m, 2H), 2.43-2.41 (m, 2H), 2.39 (s, 3H), 2.13 (s, 3H), 1.45-1.50 (m, 2H), 0.82-0.85 (m, 3H).

Example 2

Synthesis of (Z)—S-(2-(N-((4-amino-2-methylpyrimidin-5-yl) methyl) formamido)-5-(phosphonooxy) pent-2-en-3-yl) decanethioate 1-2

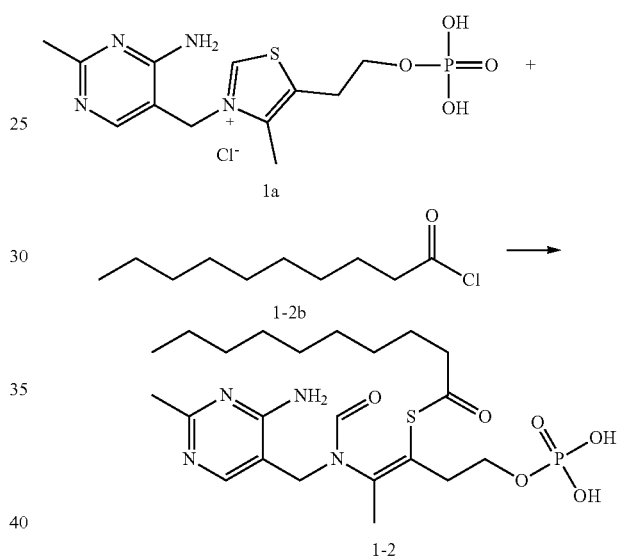

6.6 g of thiamine phosphate was dissolved in 10.0 g of water under stirring; a sodium hydroxide solution (30%) was added dropwise to adjust pH to 10-12; after stirring for 0.5 h, the pH was measured again, and adjusted to 10-12 until the pH was stable, followed by stirring for 1 h; 3.6 g of a tetrahydrofuran solution of Formula 1-2b was added dropwise over a period of time at 10° C., the mixture was reacted for 0.5 h after the addition, adjusted to pH=7-8, then extracted for liquid separation twice with ethyl acetate and once with n-heptane, adjusted to pH=7, and extracted for liquid separation once with n-heptane; dichloromethane was added, the pH was adjusted to no emulsification, the reactant was subjected to liquid separation, and drying, followed by spin-drying dichloromethane to give the product 1-2.

The product 1-2 was subjected to $^1$H NMR and MS tests, and the results were as follows. A test sample stock solution prepared from the product 1-2 was subjected to a bioassay, and the results were shown in Table 1.

MS m/z (ESI): 517.2 [M$^{+1}$]

$^1$H NMR (DMSO-d6) δ 7.99 (s, 1H), 7.81 (s, 1H), 4.47 (s, 2H), 3.82-3.81 (m, 2H), 2.59-2.51 (m, 2H), 2.43-2.42 (m, 5H), 2.41 (s, 3H), 1.45-1.44 (m, 2H), 1.28-1.22 (m, 12H), 0.87-0.84 (m, 3H).

Example 3

Synthesis of (Z)—S-(2-(N-((4-amino-2-methylpyrimidin-5-yl) methyl) formamido)-5-(phosphonooxy) pent-2-en-3-yl) dodecanethioate 1-3

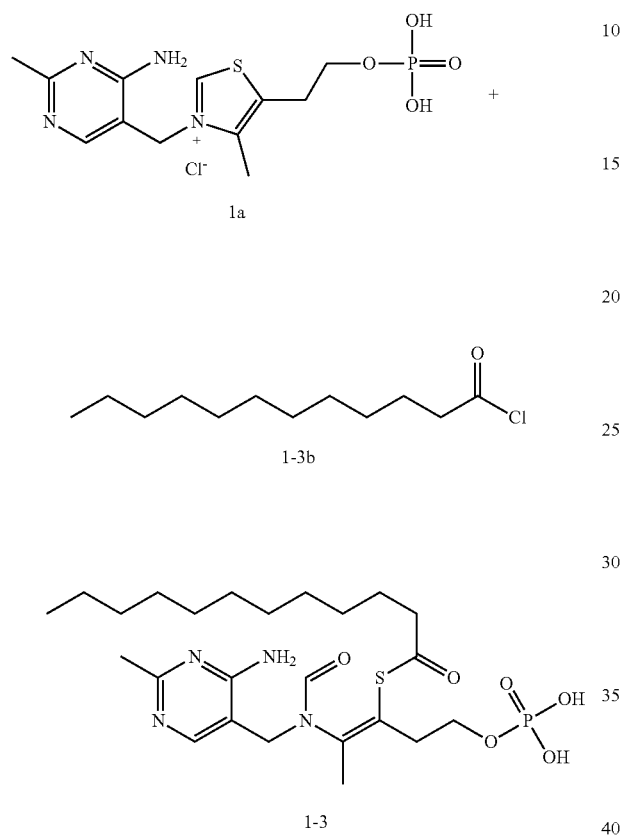

6.1 g of thiamine phosphate was dissolved in 12.8 g of water under stirring; a sodium hydroxide solution (30%) was added dropwise to adjust pH to 10-12; after stirring for 0.5 h, the pH was measured again, and adjusted to 10-12 until the pH was stable, followed by stirring for 0.5 h; a tetrahydrofuran solution of Formula 1-3b was added dropwise over a period of time at 10° C., a sodium hydroxide solution was added during the addition to maintain the pH of 10-12, and incubation was conducted for 1 h after the addition; the reactant was extracted twice with ethyl acetate, an organic phase was removed, and the pH was adjusted to 4-5 with 31% hydrochloric acid; the product was extracted with dichloromethane, a dichloromethane phase was dried over anhydrous sodium sulfate, followed by filtering, and filtrate was concentrated at 40° C. to give the product 1-3.

The product 1-3 was subjected to $^1$H NMR and MS tests, and the results were as follows. A test sample stock solution prepared from the product 1-3 was subjected to a bioassay, and the results were shown in Table 1.

MS m/z (ESI): 545.2 [M$^{+1}$]

$^1$H NMR (DMSO-d$_6$): δ 8.03 (s, 1H), 7.83 (s, 1H), 4.48 (s, 2H), 3.83-3.81 (m, 2H), 2.59 (s, 2H), 2.43-2.40 (m, 5H), 2.14 (s, 3H), 1.45-1.43 (m, 2H), 1.23-1.21 (m, 16H), 0.85 (t, 3H).

Example 4

Synthesis of (E)-S—((Z)-2-(N-((4-amino-2-methylpyrimidin-5-yl) methyl) formamido)-5-(phosphonooxy) pent-2-en-3-yl) 2-methylbut-2-enethioate 1-4

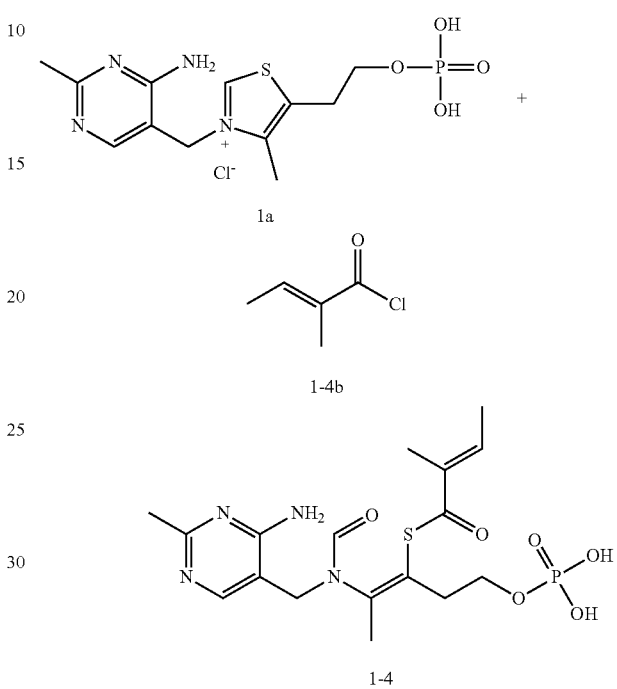

To 30 mL of dichloromethane were added 3.0 g of 2-methylbut-2-enoic acid, 0.5 g of dimethylformamide and 7.2 g of thionyl chloride, the mixture was heated under reflux for 1 h at 60° C., and distilling under reduced pressure to remove thionyl chloride and dichloromethane to obtain acyl chloride of Formula 1-4b, which was added to 30 mL of dichloromethane until use; 8.3 g of thiamine phosphate was dissolved in 18.0 g of water under stirring, a sodium hydroxide solution (30%) was added dropwise to adjust pH to 10-12, after stirring for 0.5 h, the pH was measured again, and adjusted to 10-12 until the pH was stable, followed by stirring for 0.5 h, the acyl chloride solution prepared in above steps was added dropwise over a period of time at 10° C., a sodium hydroxide solution was added during the addition to maintain the pH of 10-12, and incubation was conducted for 1 h at 10° C. after the addition; followed by distilling off dichloromethane, an aqueous phase was adjusted to pH=4-5 with 31% hydrochloric acid without precipitation, then washed twice with acetone to precipitate out the product, and filtered to obtain a filter cake, which was pulped once with ethyl acetate, then pulped with methanol twice, followed by filtered to obtain a filter cake, which was dried at 45° C. to give the product 1-4.

The product 1-4 was subjected to $^1$H NMR and MS tests, and the results were as follows. A test sample stock solution prepared from the product 1-4 was subjected to a bioassay, and the results were shown in Table 1.

MS m/z (ESI): 445.1 [M$^{+1}$]

$^1$H NMR (DMSO-d$_6$): δ 7.89 (s, 1H), 7.80 (s, 1H), 6.65 (d, 1H), 4.44 (d, 2H), 3.80-3.76 (m, 2H), 2.59 (d, 2H), 2.37 (s, 3H), 2.14 (s, 3H), 1.80-1.78 (m, 3H), 1.72-1.69 (m, 3H).

Example 5

Synthesis of (Z)—S-(2-(N-((4-amino-2-methylpyrimidin-5-yl) methyl) formamido)-5-(phosphonooxy) pent-2-en-3-yl) 2-methylbutanethioate (Product Name) 1-5

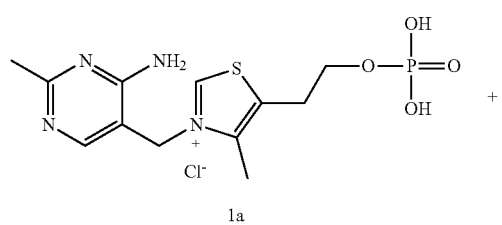

1a

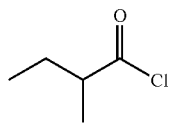

1-5b

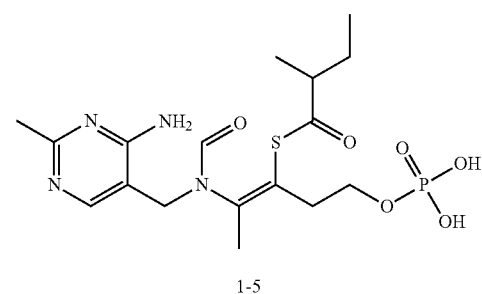

1-5

6.6 g of thiamine phosphate was dissolved in 10.0 g of water under stirring; a sodium hydroxide solution (30%) was added dropwise to adjust pH to 10-12; after stirring for 0.5 h, the pH was measured again, and adjusted to 10-12 until the pH was stable, followed by stirring for 1 h; 2.3 g of a dichloromethane solution of Formula 1-5b was added dropwise over a period of time at 10° C.; after the addition, the mixture was reacted for 1 h, and adjusted to pH=7, 50 mL of dichloromethane was added for liquid separation, an aqueous phase was adjusted to pH=2.5 to precipitate out a solid, followed by filtering, pulping with ethyl acetate for 1 h, and then filtering to obtain a filter cake, which was dried at 45° C. to give the product 1-5.

MS m/z (ESI): 447.1 [M$^{+1}$]

$^1$H NMR (DMSO-d$_6$) δ 7.96 (s, 1H), 7.77 (s, 1H), 4.47 (s, 2H), 3.81-3.77 (m, 2H), 2.60-2.53 (m, 2H), 2.47-2.46 (m, 1H), 2.41 (s, 3H), 2.14 (s, 3H), 1.54-1.51 (m, 1H), 1.37-1.36 (m, 1H), 1.03-1.00 (m, 3H), 0.84-0.79 (m, 3H).

Example 6

Synthesis of (Z)—S-(2-(N-((4-amino-2-methylpyrimidin-5-yl) methyl) formamido)-5-(phosphonooxy) pent-2-en-3-yl) 2-methylpropanethioate 1-6

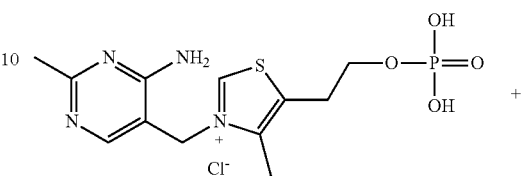

1a

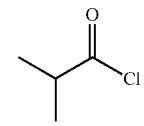

1-6b

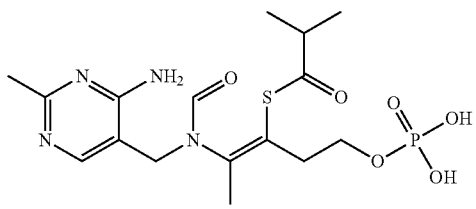

1-6

The synthetic route in Example 5 was used to give the product 1-6 by replacing starting materials 1-5b compound with 1-6b compound.

The product 1-6 was subjected to $^1$H NMR and MS tests, and the results were as follows. A test sample stock solution prepared from the product 1-6 was subjected to a bioassay, and the results were shown in Table 1.

MS m/z (ESI): 433.0 [M$^{+1}$]

$^1$H NMR (DMSO-d$_6$) δ 7.95 (s, 1H), 7.76 (s, 1H), 4.46 (s, 2H), 3.80-3.76 (m, 2H), 2.62-2.58 (m, 3H), 2.40 (s, 3H), 2.14 (s, 3H), 1.05-1.02 (m, 6H).

Example 7

Synthesis of (Z)—S-(2-(N-((4-amino-2-methylpyrimidin-5-yl) methyl) formamido)-5-(phosphonooxy) pent-2-en-3-yl) octanethioate 1-7

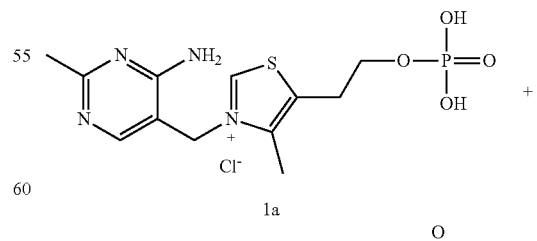

1a

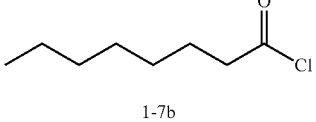

1-7b

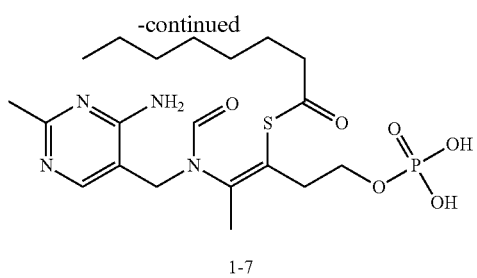

1-7

The synthetic route in Example 2 was used to give the product 1-7 by replacing starting materials 1-2b compound with 1-7b compound.

The product 1-7 was subjected to $^1$H NMR and MS tests, and the results were as follows. A test sample stock solution prepared from the product 1-7 was subjected to a bioassay, and the results were shown in Table 1.

MS m/z (ESI): 489.1 [M$^{+1}$]

$^1$H NMR (DMSO-d$_6$) δ 7.97 (s, 1H), 7.81 (s, 1H), 4.47 (s, 2H), 3.81-3.78 (m, 2H), 2.60-2.51 (m, 2H), 2.44-2.41 (m, 1H), 2.40 (s, 3H), 2.20-2.17 (m, 1H), 2.13 (s, 3H), 1.47-1.43 (m, 2H), 1.25-1.22 (m, 8H), 0.87-0.84 (m, 3H).

Example 8

Synthesis of (Z)—S-(2-(N-((4-amino-2-methylpyrimidin-5-yl) methyl) formamido)-5-(phosphonooxy) pent-2-en-3-yl) 3-phenylpropanethioate 1-8

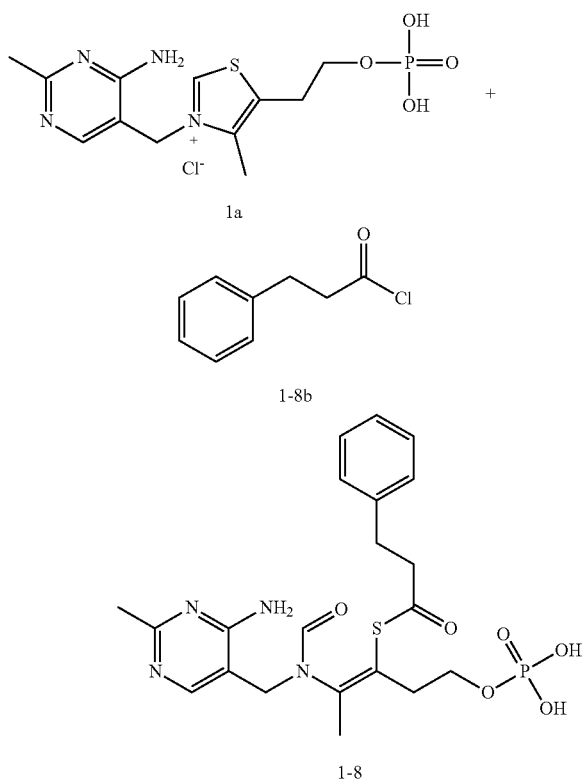

6.6 g of thiamine phosphate was dissolved in 8.8 g of water under stirring; a sodium hydroxide solution (30%) was added dropwise to adjust pH to 10-12; after stirring for 1 h, the pH was measured again, and adjusted to 10-12 until the pH was stable; a dichloromethane solution of Formula 1-8b was added dropwise over a period of time at 10° C., incubation was conducted for 1 h after the addition, followed by distilling under reduced pressure to remove dichloromethane, an aqueous phase was adjusted to pH=4 to precipitate out a solid, and filtered to obtain a filter cake, which was pulped with ethyl acetate, and filtered to give the product 1-8.

The product 1-8 was subjected to $^1$H NMR and MS tests, and the results were as follows. A test sample stock solution prepared from the product 1-8 was subjected to a bioassay, and the results were shown in Table 1.

MS m/z (ESI): 495.1 [M$^{+1}$]

$^1$H NMR (DMSO-d$_6$) δ 7.92 (s, 1H), 7.81 (s, 1H), 7.29-7.18 (m, 7H), 4.43 (s, 2H), 3.76-3.75 (m, 2H), 2.75 (m, 4H), 2.57 (s, 2H), 2.37 (s, 3H), 2.11 (s, 3H).

Example 9

Synthesis of (Z)—S-(2-(N-((4-amino-2-methylpyrimidin-5-yl) methyl) formamido)-5-(phosphonooxy) pent-2-en-3-yl) hex-5-enethioate 1-9

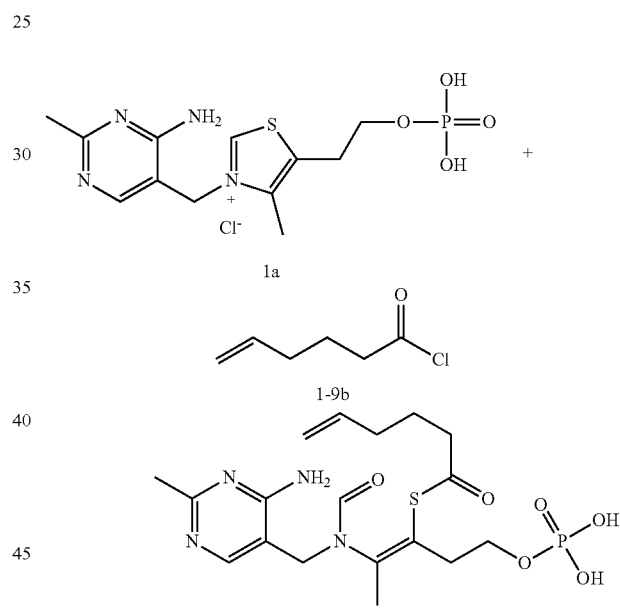

3.3 g of thiamine phosphate was dissolved in 4.4 g of water under stirring; a sodium hydroxide solution (30%) was added dropwise to adjust pH to 10-12; after stirring for 1 h, the pH was measured again, and adjusted to 10-12 until the pH was stable; a solution of acyl chloride of Formula 1-9b in tetrahydrofuran was added dropwise over a period of time at 10° C., incubation was conducted for 0.5 h after the addition, the mixture was adjusted to pH=7-8, and extracted with dichloromethane, then subjected to liquid separation, an aqueous phase was adjusted to pH=4, followed by stirring for crystallization, filtering, pulping with water for 0.5 h, and filtering to give the product 1-9.

The product 1-9 was subjected to $^1$H NMR and MS tests, and the results were as follows. A test sample stock solution prepared from the product 1-9 was subjected to a bioassay, and the results were shown in Table 1.

MS m/z (ESI): 459.1 [M$^{+1}$]

$^1$H NMR (DMSO-d$_6$) δ 7.90 (d, 1H), 7.80 (d, 1H), 5.79-5.72 (m, 1H), 5.10-5.00 (m, 2H), 4.45 (s, 2H), 3.8-3.76 (m, 2H), 2.60 (s, 2H), 2.45-2.42 (m, 2H), 2.36 (s, 3H), 2.12 (s, 3H), 2.00-1.96 (m, 2H), 1.57-1.53 (m, 2H).

Example 10

Synthesis of (Z)—S-(2-(N-((4-amino-2-methylpyrimidin-5-yl) methyl) formamido)-5-(phosphonooxy) pent-2-en-3-yl) 2-(2, 6-difluorophenyl) ethanethioate 1-10

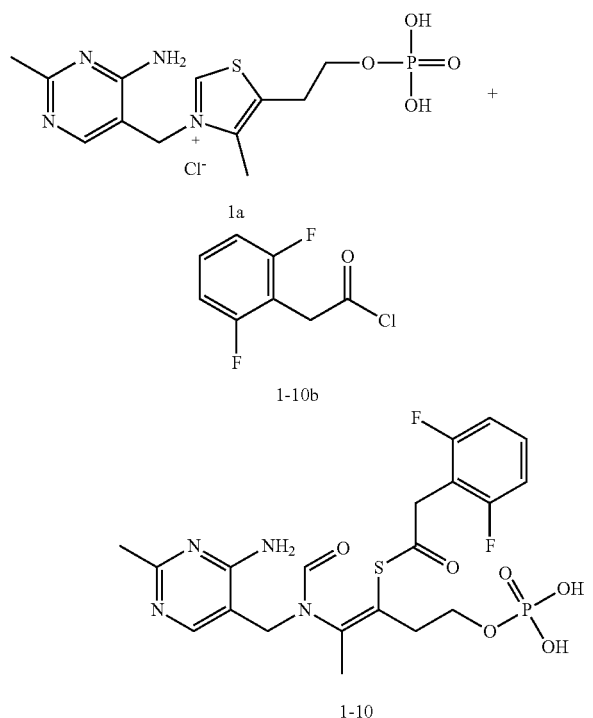

To a 100 mL single-neck flask were added 1.7 g of 2,6-difluorophenylacetic acid, 2.4 g of thionyl chloride, 0.2 g of dimethylformamide, and 30 mL of dichloromethane, the mixture was heated under reflux for 3 h at 50° C. to evaporate dichloromethane to dryness, then dissolved in tetrahydrofuran to obtain a tetrahydrofuran solution of Formula 1-10b; 2.7 g of thiamine phosphate was dissolved in 4 g of water under stirring, a sodium hydroxide solution (30%) was added dropwise to adjust pH to 10-12, after stirring for 0.5 h. the pH was measured again, and adjusted to 10-12 until the pH was stable; followed by stirring for 1 h, 1.9 g of tetrahydrofuran solution of Formula 1-10b was added dropwise over a period of time at 0° C., the mixture was adjusted to pH to 10-12, and reacted for 1 h after the addition; an aqueous phase was adjusted to pH=3-4 to precipitate out a solid, filtered to obtain a filter cake, which was pulped with methanol and water, followed by filtering to obtain a filter cake, which was dried to give the product 1-10.

The product 1-10 was subjected to $^1$H NMR and MS tests, and the results were as follows. A test sample stock solution prepared from the product 1-10 was subjected to a bioassay, and the results were shown in Table 1.

MS m/z (ESI): 517.0 [M$^{+1}$]

$^1$H NMR (DMSO-d$_6$) δ 7.85 (s, 1H), 7.76 (s, 1H), 7.47-7.40 (m, 1H), 7.13 (t, 2H), 4.43 (s, 2H), 3.87 (s, 2H), 3.90-3.76 (m, 2H), 2.60 (s, 2H), 2.34 (s, 3H), 2.11 (s, 3H).

Example 11

Synthesis of (Z)—S-(2-(N-((4-amino-2-methylpyrimidin-5-yl) methyl) formamido)-5-(phosphonooxy) pent-2-en-3-yl) 2, 2-dimethylbut-3-enethioate 1-11

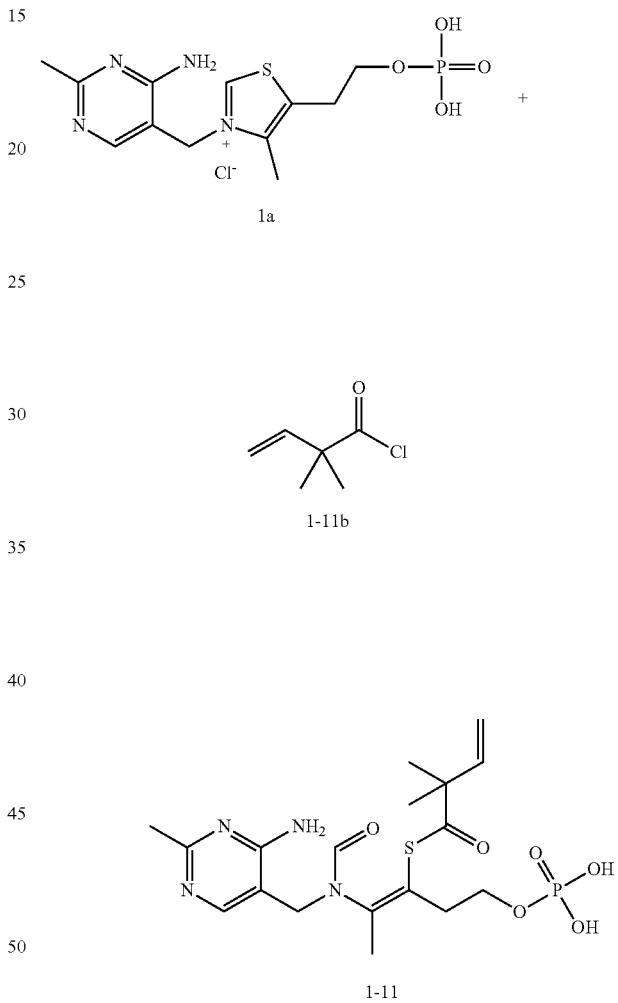

The synthetic route in Example 9 was used to give the product 1-11 by replacing starting materials 1-9b compound with 1-11b compound.

The product 1-11 was subjected to $^1$H NMR and MS tests, and the results were as follows. A test sample stock solution prepared from the product 1-11 was subjected to a bioassay, and the results were shown in Table 1.

MS m/z (ESI): 459.1 [M$^{+1}$]

$^1$H NMR (DMSO-d$_6$) δ 7.96 (s, 1H), 7.74 (s, 1H), 5.87-5.81 (m, 1H), 5.20-5.17 (m, 2H), 4.46 (s, 2H), 3.78-3.74 (m, 2H), 2.55-2.54 (m, 2H), 2.40 (s, 3H), 2.14 (s, 3H), 1.17-1.15 (m, 6H).

Example 12

Synthesis of (E)-S—((Z)-2-(N-((4-amino-2-methylpyrimidin-5-yl) methyl) formamido)-5-(phosphonooxy) pent-2-en-3-yl) hex-2-enethioate 1-12

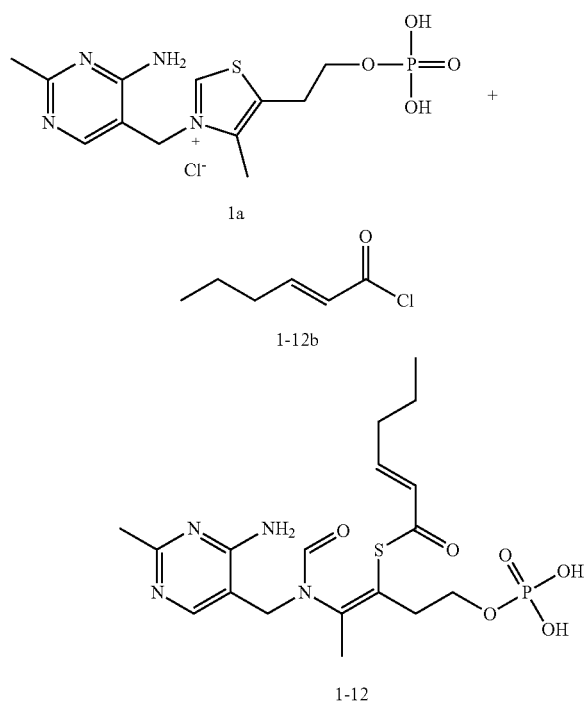

The synthetic route in Example 4 was used to give the product 1-12 by replacing starting materials 1-4b compound with 1-12b compound.

The product 1-12 was subjected to $^1$H NMR and MS tests, and the results were as follows. A test sample stock solution prepared from the product 1-12 was subjected to a bioassay, and the results were shown in Table 1.

MS m/z (ESI): 459.1 [M$^{+1}$]

$^1$H NMR (DMSO-d$_6$): δ 7.94 (s, 1H), 7.82 (s, 1H), 6.77-6.71 (m, 1H), 6.06 (d, 1H), 4.45 (d, 2H), 3.81-3.77 (m, 2H), 2.62 (d, 2H), 2.38 (s, 3H), 2.17-2.14 (m, 5H), 1.15-1.14 (m, 2H), 0.90 (t, 3H).

Example 13

Synthesis of (Z)—S-(2-(N-((4-amino-2-methylpyrimidin-5-yl) methyl) formamido)-5-(phosphonooxy) pent-2-en-3-yl) 2-ethylhexanethioate 1-13

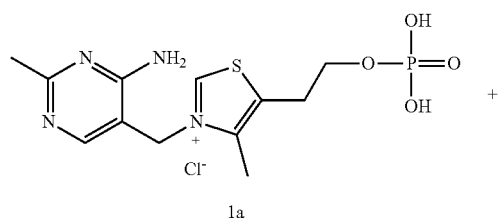

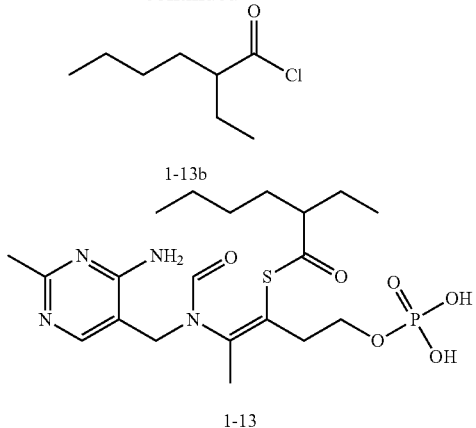

To a 50 mL single-necked flask were added 1.4 g of 2-ethylhexanoic acid, 5.0 g of thionyl chloride, 0.1 mL of dimethylformamide, and 20 mL of dichloromethane, the mixture was heated under reflux for 2 h at 55° C. to evaporate dichloromethane to dryness, then dissolved in dichloromethane to obtain a dichloromethane solution of Formula 1-13b; 3.0 g of thiamine phosphate was dissolved in 6.0 g of water under stirring, a sodium hydroxide solution (30%) was added dropwise to adjust pH to 10-12, after stirring for 0.5 h, the pH was measured again, and adjusted to 10-12 until the pH was stable; followed by stirring for 1 h, 1.44 g of dichloromethane solution of 1-13b was added dropwise over a period of time at 0° C., the mixture was adjusted to pH to 10-12, and reacted for 0.5 h after the addition, the reaction mixture was adjusted to neutral, and extracted once with ethyl acetate; an aqueous phase was adjusted to pH=3-4 to precipitate out an oily solid, and extracted with dichloromethane; after the extraction, dichloromethane was dried over anhydrous sodium sulfate, then subjected to spin-drying: the solid was dissolved in methanol, then methyl tert-butyl ether was added, the mixture was subjected to stirring 5 h to precipitate out a solid, filtered to obtain a filter cake, which was dried at 45° C. to give the product 1-13.

The product 1-13 was subjected to $^1$H NMR and MS tests, and the results were as follows. A test sample stock solution prepared from the product 1-13 was subjected to a bioassay, and the results were shown in Table 1.

MS m/z (ESI): 489.0 [M$^{+1}$]

$^1$H NMR (DMSO-d$_6$): δ 7.97 (s, 1H), 7.78 (s, 1H), 4.47 (d, 2H), 3.76-3.75 (m, 2H), 2.59 (d, 2H), 2.37 (s, 3H), 2.26 (d, 1H), 2.13 (s, 3H), 1.46-1.16 (m, 8H), 0.84-0.79 (m, 6H).

Example 14

Synthesis of (Z)—S-(2-(N-((4-amino-2-methylpyrimidin-5-yl) methyl) formamido)-5-(phosphonooxy) pent-2-en-3-yl) 2-methylpentanethioate 1-14

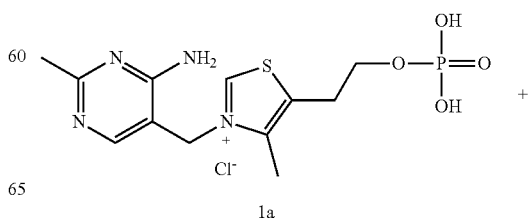

-continued

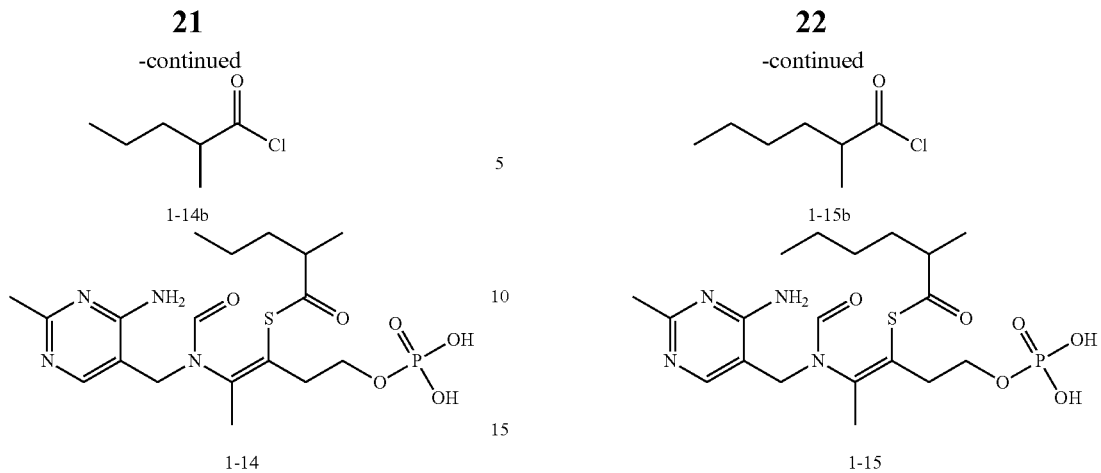

To a 100 mL single-neck flask were added 2.3 g of 2-methylvaleric acid, 4.8 g of thionyl chloride, 0.2 g of dimethylformamide, and 60 mL of dichloromethane, the mixture was heated under reflux for 3 h at 50° C. to evaporate dichloromethane to dryness, then dissolved in tetrahydrofuran to obtain a tetrahydrofuran solution of Formula 1-14b; 5.5 g of thiamine phosphate was dissolved in 8.0 g of water under stirring, a sodium hydroxide solution (30%) was added dropwise to adjust pH to 10-12, after stirring for 0.5 h, the pH was measured again, and adjusted to 10-12 until the pH was stable; followed by stirring for 1 h, 2.7 g of tetrahydrofuran solution of Formula 1-14b was added dropwise over a period of time at 0° C., the mixture s was adjusted to pH to 10-12, and reacted for 1 h after the addition; an aqueous phase was adjusted to pH=7 and extracted twice with ethyl acetate, then adjusted to pH=3-4 and extracted twice with dichloromethane; an organic phase was dried over anhydrous magnesium sulfate, then subjected to spin-drying, recrystallized from methanol and ethyl acetate, and filtered, and filter cakes were dried at 45° C. to give the product 1-14.

The product 1-14 was subjected to $^1$H NMR and MS tests, and the results were as follows. A test sample stock solution prepared from the product 1-14 was subjected to a bioassay, and the results were shown in Table 1.

MS m/z (ESI): 461.0 [M$^{+1}$]

$^1$H NMR (DMSO-d$_6$) δ 7.97 (s, 1H), 7.76 (s, 1H), 4.47 (s, 2H), 3.77 (d, 2H), 2.54 (s, 2H), 2.52 (s, 1H), 2.41 (s, 3H), 2.14 (s, 3H), 1.52-1.45 (m, 1H), 1.28-1.21 (m, 3H), 1.00 (d, 3H), 0.84 (t, 3H).

Example 15

Synthesis of (Z)—S-(2-(N-((4-amino-2-methylpyrimidin-5-yl) methyl) formamido)-5-(phosphonooxy) pent-2-en-3-yl) 2-methylhexanethioate 1-15

The synthetic route in Example 14 was used to give the product 1-15 by replacing starting materials 1-14b compound with 1-15b compound.

The product 1-15 was subjected to $^1$H NMR and MS tests, and the results were as follows. A test sample stock solution prepared from the product 1-15 was subjected to a bioassay, and the results were shown in Table 1.

MS m/z (ESI): 475.0 [M$^{+1}$]

$^1$H NMR (DMSO-d$_6$) δ 7.95 (s, 1H), 7.76 (s, 1H), 4.46 (s, 2H), 3.80-3.76 (m, 2H), 2.60 (s, 2H), 2.41 (s, 3H), 2.13 (s, 3H), 1.51-1.49 (m, 1H), 1.26-1.16 (m, 6H), 1.00 (s, 3H), 0.86 (s, 3H).

Example 16

Synthesis of (Z)—S-(2-(N-((4-amino-2-methylpyrimidin-5-yl) methyl) formamido)-5-(phosphonooxy) pent-2-en-3-yl) 2, 2-dimethylbutanethioate 1-16

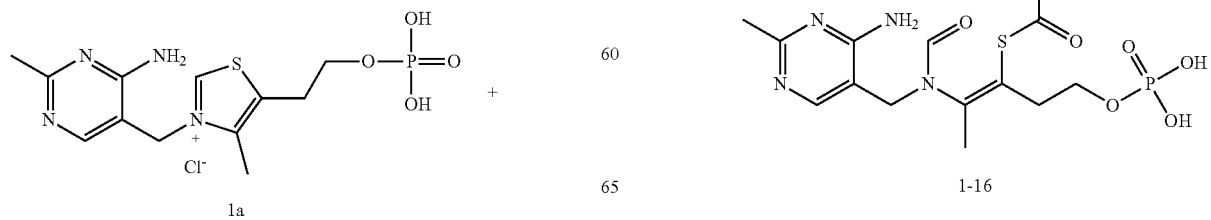

The synthetic route in Example 4 was used to give the product 1-16 by replacing starting materials 1-4b compound with 1-16b compound.

The product 1-16 was subjected to $^1$H NMR and MS tests, and the results were as follows. A test sample stock solution prepared from the product 1-16 was subjected to a bioassay, and the results were shown in Table 1.

MS m/z (ESI): 461.0 [M$^{+1}$]

$^1$H NMR (DMSO-d$_6$): δ 7.87 (s, 1H), 7.72 (s, 1H), 4.45 (d, 2H), 3.78-3.74 (m, 2H), 2.64 (d, 2H), 2.38 (s, 3H), 2.13 (s, 3H), 1.48-1.44 (m, 2H), 1.04 (s, 6H), 0.76 (t, 3H).

Example 17

Synthesis of (Z)—S-(2-(N-((4-amino-2-methylpyrimidin-5-yl) methyl) formamido)-5-(phosphonooxy) pent-2-en-3-yl) 2, 2-dimethylhexanethioate 1-17

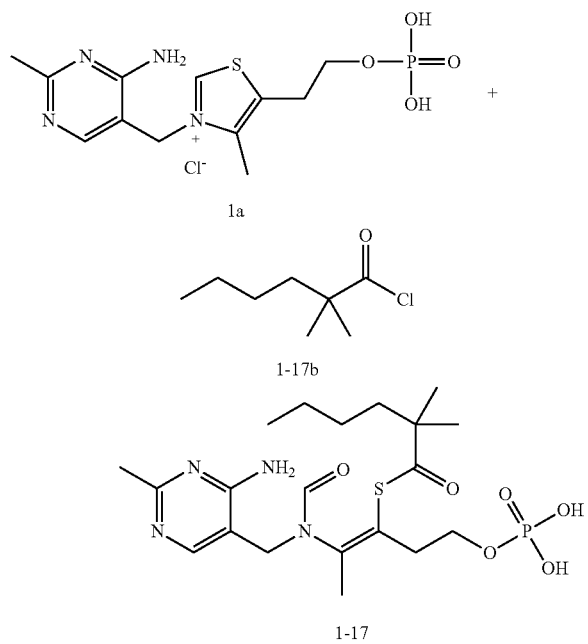

To 30 mL of dichloromethane were added 1.0 g of 2-dimethylhexanoic acid, 0.3 g of dimethylformamide and 1.7 g of thionyl chloride, the mixture was heated under reflux for 2 h at 50° C., and distilling under reduced pressure to remove thionyl chloride and dichloromethane to obtain acyl chloride of Formula 1-17b, which was added to 10 mL of tetrahydrofuran until use; 2.2 g of thiamine phosphate was dissolved in 4.4 g of water under stirring, a sodium hydroxide solution (30%) was added dropwise to adjust pH to 10-12, after stirring for 0.5 h, the pH was measured again, and adjusted to 10-12 until the pH was stable, followed by stirring for 0.5 h; the solution prepared in above steps was added dropwise over a period of time at 10° C., a sodium hydroxide solution was added during the addition to maintain the pH of 10-12, and incubation was conducted for 0.5 h at 5-10° C. after the addition; the reactant was adjusted to pH=4-5 with 31% hydrochloric acid, and extracted twice with dichloromethane; an organic phase was dried over anhydrous sodium sulfate, and concentrated to dryness under reduced pressure; the residue was pulped by adding n-heptane, the product was precipitated out, followed by filtering to obtain a filter cake, which was washed once with n-heptane, and dried under vacuum for 8 h at 50° C. to give the product 1-17.

The product 1-17 was subjected to $^1$H NMR and MS tests, and the results were as follows. A test sample stock solution prepared from the product 1-17 was subjected to a bioassay, and the results were shown in Table 1.

MS m/z (ESI): 489.0 [M$^{+1}$]

$^1$H NMR (DMSO-d$_6$): δ 8.04 (s, 1H), 7.78 (s, 1H), 4.48 (d, 2H), 3.84-3.80 (m, 2H), 2.57 (d, 2H), 2.44 (s, 3H), 2.15 (s, 3H), 1.42-1.41 (m, 2H), 1.24-1.16 (m, 4H), 1.04 (s, 6H), 0.87-0.83 (m, 3H).

Comparative Example 1

The bioassay was conducted without the addition of the test sample stock solution and with the medium as a blank control, the results of which were shown in Table 1.

Comparative Example 2

The bioassay was conducted with the test sample stock solution prepared using benfotiamine, and the results were shown in Table 1.

TABLE 1

Contents of Aβ40 and Aβ42 proteins secreted by APP/293 cells after thiamine compound treatment

| Compound | Aβ42 content (pmol/L) | Aβ40 content (pmol/L) | Compound | Aβ42 Content (pmol/L) | Aβ40 Content (pmol/L) |
|---|---|---|---|---|---|
| Example 1 | 8.59 | 45.47 | Example 2 | 5.37 | 75.15 |
| Example 3 | 4.93 | 128.90 | Example 4 | 5.77 | 71.80 |
| Example 5 | 2.09 | 37.65 | Example 6 | 2.41 | 44.38 |
| Example 7 | 6.09 | 106.81 | Example 8 | 6.38 | 57.86 |
| Example 9 | 5.70 | 80.40 | Example 10 | 10.62 | 71.11 |
| Example 11 | 3.22 | 54.75 | Example 12 | 0.34 | 32.87 |
| Example 13 | 24.36 | 56.28 | Example 14 | 6.79 | 60.34 |
| Example 15 | 9.59 | 40.39 | Example 16 | 33.70 | 85.96 |
| Example 17 | 6.24 | 77.22 | Comparative Example 1 | 11.08 | 127.81 |
| Comparative Example 2 | 5.04 | 53.77 | | | |

According to the above experimental results, compared with the blank in Comparative Example 1, all the compounds of the structured have inhibitory effects on Aβ42 or/and Aβ40 compared with benfotiamine in Comparative Example 2, the content of Aβ40 in Example 11 is substantially the same as that in Comparative Example 2, but the content of Aβ42 is reduced, indicating a better inhibitory effect on Aβ42; compared with benfotiamine in Comparative Example 2, in Examples 5, 6, and 12, especially in Example 12, the contents of Aβ40 and Aβ42 are significantly reduced, indicating a greater enhancement of inhibitory effects on Aβ40 and Aβ42.

Although the present invention is disclosed above, the present invention is not limited thereto. Any person skilled in the art can make various changes and modifications without departing from the spirit and scope of the present invention. Therefore, the protection scope of the present invention should be subject to the scope defined by the claims.

The invention claimed is:

1. A thiamine compound or a stereoisomer thereof or salts of the thiamine compound or the stereoisomer thereof, having a structure as shown in Formula (1) or Formula (2),

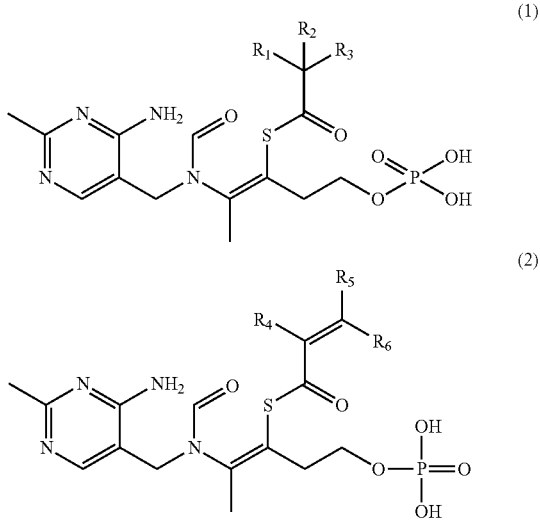

wherein $R_1$, $R_2$, $R_3$, $R_4$, $R_5$ and $R_6$ are each independently hydrogen atom, halogen atom, nitro, cyano, sulfo, amino, substituted amine group, ester group, carboxyl, hydroxyl, sulfydryl, hydrocarbylsulfydryl, hydrocarbyl, substituted hydrocarbyl, hydrocarbyloxy, substituted hydrocarbyloxy, acyl or acylamino;

wherein not all of $R_1$, $R_2$ and $R_3$ are hydrogen atom;

wherein the hydrocarbyl is selected from methyl, vinyl, propenyl, n-propyl, isopropyl, n-butyl, t-butyl, isobutyl, pentyl, 1-ethylpropyl, 1-methylbutyl, cyclopentyl, hexyl, 1-methylpentyl, 1-ethylbutyl, cyclohexyl, 2-heptyl, heptyl, octyl, nonyl, undecyl, dodecyl, tridecyl, pentadecyl, heptadecyl, octadecyl, nonadecyl, eicosyl, heneicosyl, docosyl, tricosyl, 2-methylphenyl, 3-methylphenyl, 4-methylphenyl, 1-naphthyl, 2-naphthyl, benzyl and 2-phenylethyl; and wherein the substituted hydrocarbyl is selected from halogen atom substitution, nitro substitution, cyano substitution, sulfo substitution, amine substitution, carboxyl substitution, hydroxyl substitution and sulfydryl substitution of the above-mentioned hydrocarbyl.

2. A thiamine compound or a stereoisomer thereof or salts of the thiamine compound or the stereoisomer thereof, having a structure as shown in Formula (1),

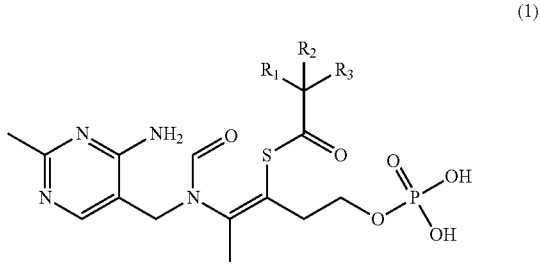

wherein $R_1$ and $R_2$ are hydrogen atom, and $R_3$ is benzyl or 1,5-difluorophenyl.

3. The thiamine compound according to claim 1, wherein $R_1$, $R_2$, $R_3$, $R_4$, $R_5$ and $R_6$ are each independently hydrogen atom or C1-C18 hydrocarbyl;

wherein not all of $R_1$, $R_2$ and $R_3$ are hydrogen atom; and wherein the C1-C18 hydrocarbyl is selected from methyl, vinyl, propenyl, n-propyl, isopropyl, n-butyl, t-butyl, isobutyl, pentyl, 1-ethylpropyl, 1-methylbutyl, cyclopentyl, hexyl, 1-methylpentyl, 1-ethylbutyl, cyclohexyl, 2-heptyl, heptyl, octyl, nonyl, undecyl, dodecyl, tridecyl, pentadecyl, heptadecyl, octadecyl, 2-methylphenyl, 3-methylphenyl, 4-methylphenyl, 1-naphthyl, 2-naphthyl, benzyl and 2-phenylethyl.

4. A thiamine compound or a stereoisomer thereof or salts of the thiamine compound or the stereoisomer thereof, having a structure as shown in Formula (1),

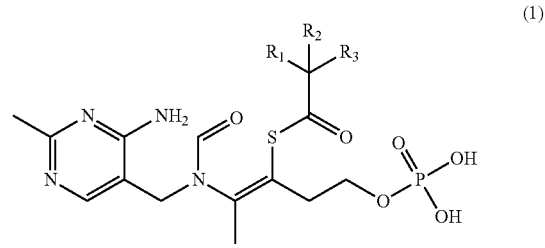

wherein $R_1$ and $R_2$ are each independently hydrogen atom, methyl or ethyl, and $R_3$ is C1-C10 hydrocarbyl; and wherein the C1-C10 hydrocarbyl is selected from methyl, vinyl, propenyl, n-propyl, isopropyl, n-butyl, t-butyl, isobutyl, pentyl, 1-ethylpropyl, 1-methylbutyl, cyclopentyl, hexyl, 1-methylpentyl, 1-ethylbutyl, cyclohexyl, 2-heptyl, heptyl, octyl, nonyl, 2-methylphenyl, 3-methylphenyl, 4-methylphenyl, 1-naphthyl, 2-naphthyl, benzyl and 2-phenylethyl.

5. The thiamine compound according to claim 4, wherein $R_1$ is hydrogen atom, $R_2$ is methyl or ethyl, and $R_3$ is methyl.

6. The thiamine compound according to claim 4, wherein $R_1$ is methyl, $R_2$ is methyl, and $R_3$ is vinyl.

7. The thiamine compound according to claim 3, wherein the thiamine compound has the structure as shown in Formula (2), $R_4$ and $R_5$ are hydrogen atom, and $R_6$ is n-propyl.

8. A pharmaceutical composition comprising the thiamine compound according to claim 1 or a stereoisomer thereof or salts of the thiamine compound or the stereoisomer thereof.

9. A method for treating Alzheimer's disease, comprising administering to a subject in need thereof a pharmaceutical composition according to claim 8.

10. A pharmaceutical composition comprising the thiamine compound according to claim 2 or a stereoisomer thereof or salts of the thiamine compound or the stereoisomer thereof.

11. A pharmaceutical composition comprising the thiamine compound according to claim 4 or a stereoisomer thereof or salts of the thiamine compound or the stereoisomer thereof.

12. A method for treating Alzheimer's disease, comprising administering to a subject in need thereof a pharmaceutical composition according to claim 10.

13. A method for treating Alzheimer's disease, comprising administering to a subject in need thereof a pharmaceutical composition according to claim 11.

* * * * *